United States Patent
Marker et al.

(10) Patent No.: US 9,963,399 B2
(45) Date of Patent: May 8, 2018

(54) PROCESS FOR CONVERSION OF METHANE TO HIGHER HYDROCARBONS, INCLUDING LIQUID FUELS

(71) Applicant: GAS TECHNOLOGY INSTITUTE, Des Plaines, IL (US)

(72) Inventors: Terry Marker, Palos Heights, IL (US); Martin Linck, Roscoe, IL (US); Jim Wangerow, Oak Park, IL (US); Pedro Ortiz-Toral, Wheeling, IL (US); Naomi Klinghoffer, Chicago, IL (US)

(73) Assignee: Gas Technology Institute, Des Plaines, IL (US)

( * ) Notice: Subject to any disclaimer, the term of this patent is extended or adjusted under 35 U.S.C. 154(b) by 81 days.

(21) Appl. No.: 15/288,329

(22) Filed: Oct. 7, 2016

(65) Prior Publication Data

US 2017/0101352 A1 Apr. 13, 2017

Related U.S. Application Data

(60) Provisional application No. 62/238,201, filed on Oct. 7, 2015, provisional application No. 62/310,889, filed on Mar. 21, 2016.

(51) Int. Cl.
*C07C 2/74* (2006.01)
*C07C 1/00* (2006.01)
(Continued)

(52) U.S. Cl.
CPC .............. *C07C 1/00* (2013.01); *C01B 3/34* (2013.01); *C07C 1/322* (2013.01); *C07C 2/86* (2013.01)

(58) Field of Classification Search
CPC ....................................................... C07C 2/74
(Continued)

(56) References Cited

U.S. PATENT DOCUMENTS

| 4,451,685 A | 5/1984 | Nevitt et al. |
| 4,480,143 A | 10/1984 | Chang et al. |

(Continued)

OTHER PUBLICATIONS

Zhu, Q. et al., "Sulfur as a selective 'soft' oxidant for catalytic methane conversion probed by experiment and theory", Nature Chemistry, vol. 5, pp. 104-109, (Dec. 2012).

(Continued)

*Primary Examiner* — Thuan D Dang
(74) *Attorney, Agent, or Firm* — Banner & Witcoff, Ltd.

(57) ABSTRACT

Aspects of the invention are associated with the discovery of processes for converting methane ($CH_4$), present in a methane-containing feedstock that may be obtained from a variety of sources such as natural gas, to higher hydrocarbons (e.g., $C_4^+$ hydrocarbons) such as gasoline, diesel fuel, or jet fuel boiling-range hydrocarbons, which may optionally be separated (e.g., by fractionation) for use as transportation fuels, or otherwise as blending components for such fuels. Particular aspects of the invention are associated with advantages arising from maintaining reaction conditions that improve the yield of $C_4^+$ hydrocarbons. Further aspects relate to the advantages gained by integration of the appropriate reactions to carry out the methane conversion, with downstream separation to recover and recycle desirable components of the reaction effluent, thereby improving process economics to the extent needed for commercial viability.

15 Claims, 2 Drawing Sheets

(51) Int. Cl.
  *C01B 3/34* (2006.01)
  *C07C 2/86* (2006.01)
  *C07C 1/32* (2006.01)

(58) Field of Classification Search
  USPC .............................. 585/943, 901, 903, 315
  See application file for complete search history.

(56) References Cited

U.S. PATENT DOCUMENTS

| | | |
|---|---|---|
| 4,543,434 A | 9/1985 | Chang |
| 4,822,938 A | 4/1989 | Audeh et al. |
| 4,864,074 A | 9/1989 | Han et al. |
| 5,043,505 A | 8/1991 | Erekson et al. |
| 8,915,981 B2 | 12/2014 | Marker et al. |

OTHER PUBLICATIONS

Quann, R.J.. et al., "Chemistry of Olefin Oligomerization over ZSM-5 Catalyst", Ind. Eng. Chem. Res., vol. 27(4), pp. 565-570, (1988).

Fukuda, K. et al., "Catalytic Decomposition of Hydrogen Sulfide", Ind. Eng. Chem. Fundam., vol. 17(4), pp. 243-248 (1978).

Hosseini, H. et al., "Carbon Disulfide Production via Hydrogen Sulfide Methane Reformation", International Scholarly and Scientific Research & Innovation, vol. 4(2), pp. 198-201 (2010).

Erekson, E.J. "Gasoline From Natural Gas by Sulfur Processing", Technical Report, Work Performed Under Contract No. DE-AC22-93PC92114, (Jul. 1996).

PROCESS FOR CONVERSION OF METHANE TO HIGHER HYDROCARBONS, INCLUDING LIQUID FUELS

CROSS-REFERENCE TO RELATED APPLICATIONS

This application claims priority to U.S. provisional application No. 62/238,201, filed Oct. 7, 2015, and to U.S. provisional application No. 62/310,889, filed Mar. 21, 2016, both of which applications are hereby incorporated by reference in their entireties.

FIELD OF THE INVENTION

Aspects of the invention relate to processes and systems for the soft oxidation of methane (i.e., reaction of methane with a sulfur-containing compound as opposed to oxygen) to produce higher hydrocarbons, and more particularly $C_4^+$ hydrocarbons that may be used in transportation fuels or as chemicals.

DESCRIPTION OF RELATED ART

The ongoing search for alternatives to crude oil, for the production of hydrocarbon fuels and specialty chemicals (e.g., petrochemical precursors such as olefins and aromatics), is increasingly driven by a number of factors. These include diminishing petroleum reserves, higher anticipated energy demands, and heightened concerns over greenhouse gas (GHG) emissions from sources of non-renewable carbon. In view of its abundance in natural gas reserves, methane has become the focus of a number of possible synthesis routes. Known commercial processes for converting natural gas into liquid fuels include Fisher-Tropsch (FT) synthesis and those involving the formation of methanol as an intermediate for subsequent dehydration, i.e., in methanol-to-gasoline (MTG) conversion. Whereas these methods are widely used and improve the economics of transporting natural gas over long distances, they nonetheless involve considerable complexity, capital expenditure, and multiple conversion steps. These known methods also suffer from poor selectively to gasoline boiling-range hydrocarbons and result in the production of carbon dioxide. Furthermore, both FT and MTG processes require pretreatment of the feedstock for $H_2S$ removal, in order to obtain acceptable catalyst stability.

The oxidation of methane with $O_2$ to directly produce hydrocarbons and $H_2O$, while studied extensively, has been met with a number of significant challenges. These include thermodyamically favorable reaction pathways that lead to further oxidation ("over oxidation") of the desired hydrocarbons and oxygenates, resulting in substantial $CO_2$ formation. In addition, management of the highly exothermic oxidation reaction poses a number of practical problems in terms of process design. The catalytic, oxidative coupling of methane and other hydrocarbons to form higher hydrocarbons is described, for example in U.S. Pat. No. 5,043,505.

In comparison, the free energy losses associated with the counterpart reactions using $S_2$ versus $O_2$ as a reactant with methane, including over oxidation reactions, are significantly lower. This has led to the characterization of sulfur-based methane conversion as "soft oxidation." The study of various catalysts for the conversion of $CH_4$ and elemental sulfur to $CS_2$ and hydrocarbons is documented, for example, in Zhu, Q. et al. (NATURE CHEMISTRY, Vol. 5 (December 2012): 104-109). Other publications disclosing the production of $CS_2$ from methane and sulfur include U.S. Pat. No. 4,480,143; U.S. Pat. No. 4,543,434; U.S. Pat. No. 4,822,938; and U.S. Pat. No. 4,864,074, which also describe further processing steps to obtain higher hydrocarbons such as aromatics. See also Quann, R. J. et al. (IND. ENG. CHEM. RES., Vol. 27(4) (1988): 565-570) and U.S. Pat. No. 4,451,685. The use of $S_2$ over $O_2$ has therefore been investigated as a route to hydrocarbon production, in which the product selectivity and process thermodynamics are more easily managed. In addition, methods for obtaining elemental sulfur as a necessary starting material are practiced industrially as the Claus process, or are otherwise known from, for example, Fukuda, K. et al. (IND. ENG. CHEM. FUNDAM., VOL 17(4) (1978): 243-248). Sulfur is also a less expensive oxidant than oxygen, since oxygen must be initially separated from nitrogen for use.

More recently, the use of $H_2S$, rather than elemental sulfur, has been investigated as the reactant for catalytically converting $CH_4$ to $CS_2$. See Hosseini, H. et al. (INTERNATIONAL SCHOLARLY AND SCIENTIFIC RESEARCH & INNOVATION, Vol. 4(2) (2010): 198-201). An additional downstream, catalytic reaction of the $CS_2$, as part of a two-step hydrogen sulfide methane ("HSM") process for producing hydrocarbons, is discussed in Erekson, E. J. (Work Performed Under Contract No.: DE-AC22-93PC92114 (July 1996)). In order for processes that synthesize liquid hydrocarbons (e.g., gasoline and jet fuel) from methane to advance to the point of economic feasibility, a number of factors must be addressed, particularly in terms of product yields and process integration steps that limit the losses of valuable reactants and intermediates.

SUMMARY OF THE INVENTION

Aspects of the invention are associated with the discovery of processes for converting methane ($CH_4$), present in a methane-containing feedstock, which may be obtained from a variety of sources such as natural gas, to higher hydrocarbons (e.g., $C_4^+$ hydrocarbons). These higher hydrocarbons include gasoline, diesel fuel, or jet fuel boiling-range hydrocarbons, which may optionally be separated (e.g., by fractionation) from liquid products of the processes. In addition to separation, or alternatively, these higher hydrocarbons or their separated fractions may be further reacted for use as (i) transportation fuels, (ii) blending components for such fuels, (iii) viscosity-reducing agents to enhance transportability of other hydrocarbon fractions, and/or (iv) specialty chemicals such as aromatic hydrocarbons (e.g., para-xylene). Particular aspects of the invention are associated with advantages arising from maintaining reaction conditions that improve the selectivity to, and/or yield of $C_4^+$ hydrocarbons over a given stage or reactor. For example, in the case of methane being predominantly reacted, such as converted to an intermediate (e.g., $CS_2$), in one reaction step or stage, conventional considerations regarding process design would suggest that the most efficient location for introduction of all of the methane-containing feedstock would be an inlet to this reaction step or stage, or at least a point upstream of this reaction step or stage (i.e., without any intervening separation or reaction vessels, prior to the reaction step or stage). In contrast, according to embodiments of the invention, discussed in greater detail below, introducing the methane-containing feedstock at one or more other introduction locations has important implications with respect to influencing reaction selectivity and yield in other parts of the process, such as a reaction step or stage to convert the intermediate, produced in the first stage, to the $C_4^+$ hydrocarbons. In particular embodiments, at least part, and preferably substantially all, of the methane-containing feedstock is fed to an inlet of a reaction step or stage, or a point upstream of this reaction step or stage, which is not the reaction step or stage used predominantly to convert methane to an intermediate (e.g., $CS_2$).

More specifically, by feeding at least a portion of the methane-containing feedstock to a reaction step or stage, or upstream of such reaction step or stage, predominantly for conversion of the intermediate to $C_4^+$ hydrocarbons, important reaction conditions may be established in this conversion, such as a desired methane partial pressure. By maintaining sufficient methane partial pressure, undesired reactions such as methane re-formation may be advantageously suppressed, leading to an increase in the selectivity to, and/or yield of $C_4^+$ hydrocarbons. Accordingly, the process may be operated with a sufficient methane partial pressure in a reaction step or stage predominantly to convert the intermediate to higher hydrocarbons, with, or possibly even without, feeding at least a portion of the methane-containing feedstock to this reaction step or stage, or upstream of this reaction step or stage. Advantageously, an increase in the yield of higher hydrocarbons, across a particular reaction step or stage of the process, reduces the amount of materials being recycled, as well as the amount of materials being heated to the substantial reaction temperatures needed to convert methane to an intermediate. Therefore, both process equipment costs and operating costs are reduced.

Further aspects of the invention relate to the advantages gained by integration of the appropriate reactions to carry out the methane conversion, with downstream separation to recover and recycle desirable components of the reaction effluent, thereby improving process economics to the extent needed for commercial viability. According to one important aspect, $H_2S$, which is a reactant with $CH_4$, may be separated (together with unconverted $CH_4$) from the reaction effluent (e.g., separated from a vapor product of this effluent) and recycled. This leads to particular advantages if two or more reaction steps or stages in the overall process lead to the conversion of methane to higher hydrocarbons, and $H_2S$ is consumed in one reaction step or stage but produced in another reaction step or stage. In this case, the $H_2S$ may be continually recycled, and only very small rate of $H_2S$ addition is required to sustain the process, for example to make up for losses in a bleed (vent or purge) gas stream or in a net hydrogen production stream, and/or otherwise losses by dissolution in a liquid hydrocarbon product (e.g., comprising some or all of the higher hydrocarbons produced).

Processes described herein therefore perform the "soft oxidation" of methane, i.e., at least one reaction step or stage of the process is predominantly to convert methane by reaction with sulfur or a sulfur-containing compound (e.g., $H_2S$), in a reaction stage or step that leads to the overall conversion to higher hydrocarbons that may be a source of a variety of products. These products may include "drop in" gasoline and/or diesel fuel, or otherwise may include chemicals such as aromatic hydrocarbons (e.g., benzene, toluene, and/or xylenes), potentially having a higher value relative to hydrocarbon fuels. The processes may have a number of practical applications, including the conversion of stranded natural gas, for example if the process is made portable by mounting on a skid. Without access to a suitable source for conversion to value-added products, such stranded natural gas might otherwise be flared (combusted), with the accompanying generation of $CO_2$. Accordingly, processes described herein can effectively monetize otherwise unusable sources of natural gas, with the added benefit of reducing greenhouse gas emissions. Moreover, if the methane-containing feedstock is obtained from a renewable resource (e.g., biomass), for example by hydropyrolysis as described in U.S. Pat. No. 8,915,981 assigned to Gas Technology Institute, then processes described herein may be used to provide renewable hydrocarbon-containing fuels, fuel blending components, and/or chemicals. The overall carbon footprint associated with the production of the higher hydrocarbons, e.g., based on a lifecycle assessment of their greenhouse gas (GHG) emissions, may be further reduced if at least a portion of the hydrogen product is combusted to provide some or all of the heating requirements of the process (e.g., by transferring combustion heat to the process recycle gas or to the methane-containing feedstock). By combusting hydrogen product, the process may be sustained, at least in terms of its heating requirements, without the release of $CO_2$ into the environment.

Soft oxidation processes described herein may convert, in a first stage, substantially all of the methane in a methane-containing feedstock to reactive carbon disulfide, advantageously without the need for solid sulfur as a reactant. The processes may additionally include the conversion of carbon disulfide ($CS_2$) at economically favorable selectivity to $C_4^+$ hydrocarbons (i.e., higher hydrocarbons having four carbon atoms or more), in a second stage. Improvements in both selectivity and yield (the product of conversion and selectivity) of the $C_4^+$ hydrocarbons in the second stage may be achieved by suppressing or largely avoiding the undesirable re-formation of methane. Moreover, the processes may be advantageously operated without the release of any significant amounts of carbon dioxide, sulfur, and/or sulfur-containing compounds to the environment. As described above, the required sulfur, in the form of $H_2S$, may be consumed and regenerated in first and second process stages, respectively, as well as recycled continuously without any significant overall consumption or production. In one sense, the $H_2S$ acts as a gas phase "catalyst," that is consumed in the process to only a very minimal extent, e.g., as needed to replace trace amounts in gas and liquid products. Overall, therefore, in representative embodiments, (i) all or substantially all of the carbon of the methane, initially present in the methane-containing feedstock, is converted to higher hydrocarbons present in the liquid product, (ii) all or substantially all of the hydrogen, initially present in the methane-containing feedstock, is converted to $H_2$ present in a hydrogen product stream, or a net hydrogen production stream, as described herein, (iii) all or substantially all of the $H_2S$, used as a reactant in a first stage, is regenerated in a second stage and recycled, and/or (iv) all or substantially all of methane that is not converted in a given pass through the first and second stages is recycled to extinction.

According to particular processes, sulfur oxidation of methane in a first stage is combined with vapor phase hydrogenation/oligomerization of $CS_2$ in a second stage. Suppression of the undesirable re-formation of methane in the second stage may be achieved using second stage operating conditions that include a sufficient methane partial pressure. For example, methane partial pressure can be increased if all, or substantially all, of the methane-containing feedstock is introduced to an inlet to the second stage, or to a point of mixing with the effluent of the first stage. The increased methane partial pressure in the second stage, compared to a base-case operation in which all of the methane-containing feedstock is introduced to the first stage (e.g., at an inlet to a sulfur oxidation reactor used in this stage) where it is predominantly consumed, improves selectivity to $C_4^+$ hydrocarbons in the second stage, relative to this base-case operation. Process economics are thereby improved considerably, as recycle compressor power, heating and cooling duties, and equipment sizes, are reduced. Accordingly, disclosed herein are processes for the commercially viable production of hydrocarbon fuels from methane, using soft oxidation.

These and other embodiments, aspects, and advantages relating to the present invention are apparent from the following Detailed Description.

BRIEF DESCRIPTION OF THE DRAWINGS

A more complete understanding of the exemplary embodiments of the present invention and the advantages thereof may be acquired by referring to the following description in consideration of the accompanying figures, in which the same reference numbers are used to identify the same features.

Figure 1:
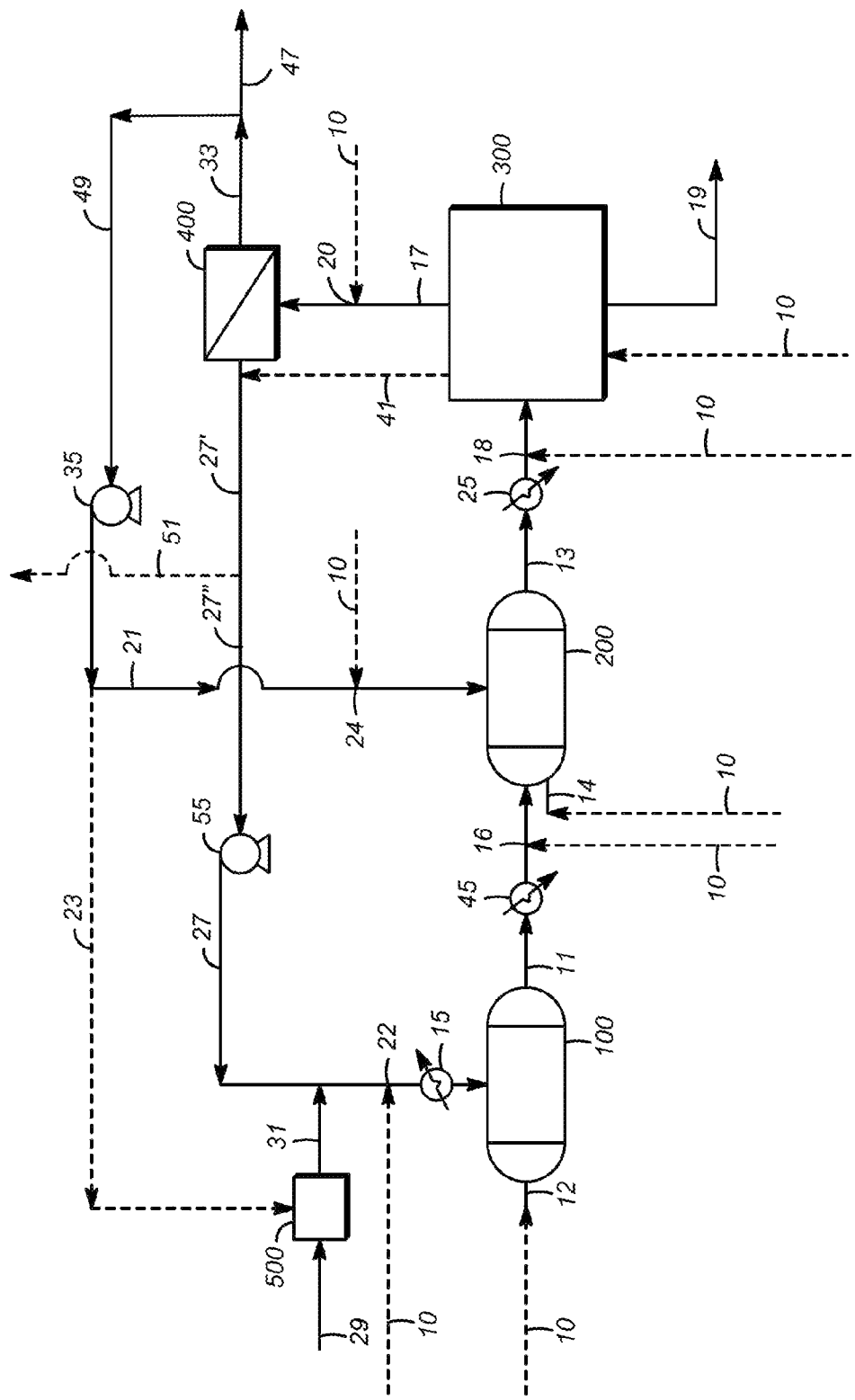
FIG. 1 depicts a flowscheme that illustrates a representative two-stage process as described herein.
Figure 2:
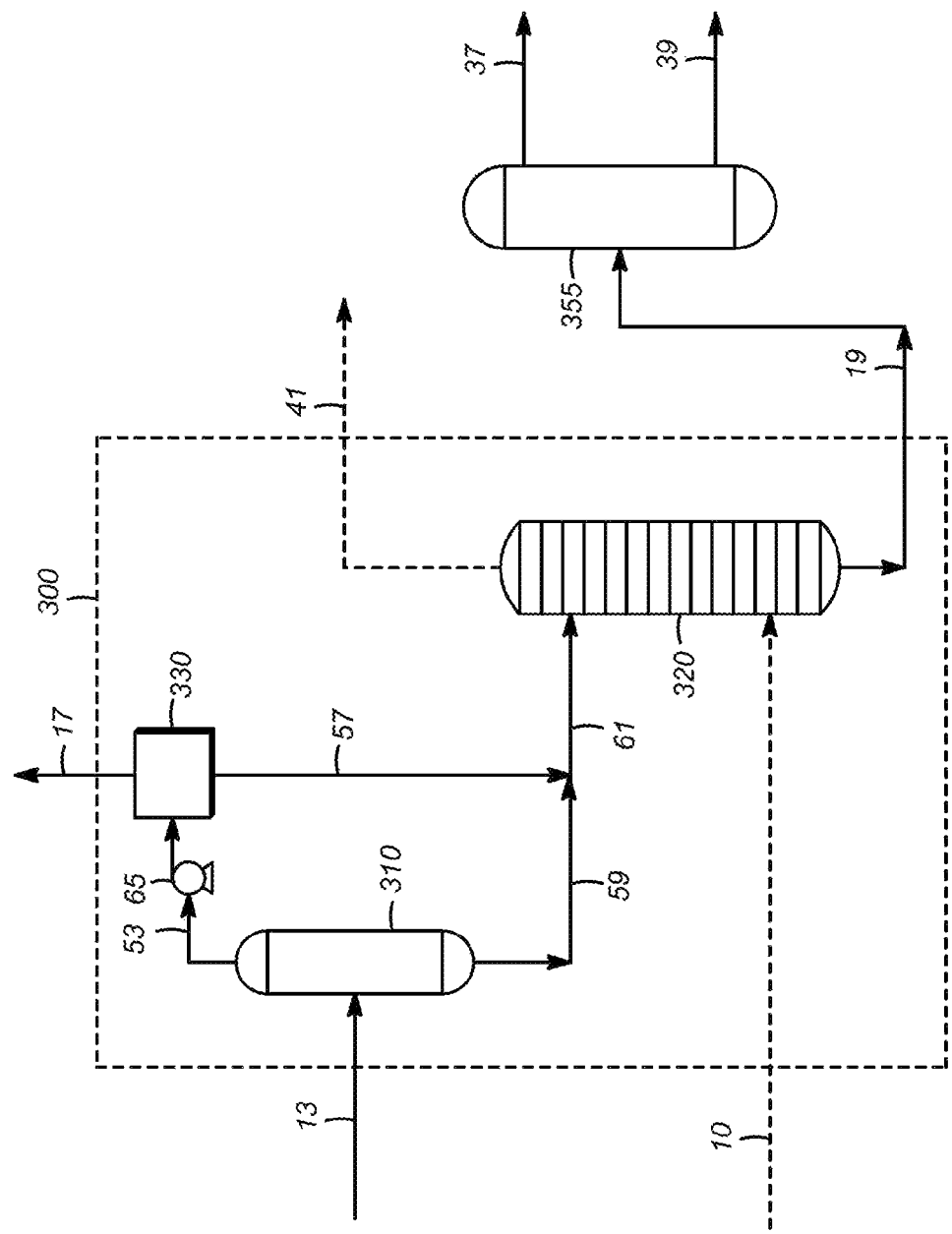
FIG. 2 depicts flowscheme that illustrates a separation stage that may be used in a process as described herein.

The figures should be understood to present an illustration of the disclosure and/or principles involved. In order to facilitate explanation and understanding, simplified equipment is depicted in FIGS. 1 and 2, and these figures are not necessarily drawn to scale, such that some components and structures, as well details pertaining to their configurations, may be exaggerated. Valves, instrumentation, and other equipment and systems not essential to the understanding of the various aspects of the invention are not shown. As is readily apparent to one of skill in the art having knowledge of the present disclosure, processes for converting a methane-containing feedstock to higher hydrocarbons, will have configurations and components determined, in part, by their specific use.

DETAILED DESCRIPTION

Embodiments of the invention relate to a process for converting a methane-containing feedstock to higher hydrocarbons (e.g., $C_4^+$ hydrocarbons). Representative methane-containing feedstocks are gases comprising at least 50% (e.g., from 50% to more than 99%) $CH_4$, with such gases typically comprising at least 75% (e.g., from 75% to more than 99%) $CH_4$, and often comprising at least 90% (e.g., from 90% to more than 99%) $CH_4$. Methane-containing feedstocks may include gaseous hydrocarbon impurities such as ethane and propane, as well as non-hydrocarbon impurities such as CO and $CO_2$. Advantageously, because $H_2S$ is present in the process, the methane-containing feedstock may contain this sulfur-containing compound, without concerns relating to its detrimental effect as a catalyst poison in known processes, such as FT synthesis and MTG conversion, referenced above. Accordingly, in some embodiments, the methane-containing feedstock may include $H_2S$ in a concentration of at least 500 parts per million by volume (vol-ppm), at least 0.1% by volume (vol-%), or even at least 1 vol-%.

An important methane-containing feedstock is natural gas, and particularly stranded natural gas, which, using known processes, cannot be economically upgraded to $C_4^+$ hydrocarbons. Other methane-containing feedstocks may be obtained from coal or biomass (e.g., char) gasification, from a biomass digester, or as effluents from biofuel production processes (e.g., pyrolysis processes and fatty acid/triglyceride hydroconversion processes). The methane may therefore be derived from a renewable carbon source. Other sources of methane-containing feedstocks include effluents of industrial processes such as steel manufacturing processes or non-ferrous product manufacturing processes. Further sources include effluents of petroleum refining processes, electric power production processes, chemical (e.g., methanol) production processes, and coke manufacturing processes.

Processes described herein convert methane, in one or more reaction stages or steps, to higher hydrocarbons, which may be recovered (e.g., by condensation) into a liquid product. The higher hydrocarbons may also be further separated into desired fractions using one or more separation steps, such as on the basis of relative volatility (e.g., by a single vapor-liquid equilibrium stage of flashing or by multiple vapor-liquid equilibrium stages of distillation, either of which may optionally be performed with a stripping gas). A representative fraction is $C_4^+$ hydrocarbons, although this fraction may also be the entire liquid product recovered from a final (e.g., the second) reaction step or stage of the process, without further separation. Other representative fractions include $C_4$-$C_{10}$ hydrocarbons, $C_6$-$C_{10}$ hydrocarbons, and other fractions of the higher hydrocarbons produced from the process. Commercially relevant fractions, in the case of transportation fuels, include those comprising (i) predominantly, or substantially all, naphtha or gasoline boiling-range hydrocarbons (i.e., a gasoline fraction), (ii) predominantly, or substantially all, diesel fuel boiling-range hydrocarbons (i.e., a diesel fuel fraction), or (iii) predominantly, or substantially all, jet fuel boiling-range hydrocarbons (i.e., a jet fuel fraction). Naphtha or gasoline boiling-range hydrocarbons may have an initial boiling point (or "front-end") temperature characteristic of $C_5$ hydrocarbons, for example from about 30° C. (86° F.) to about 40° C. (104° F.), with a representative value being 35° C. (95° F.) and a distillation end point temperature generally from 110° C. (230° F.) to about 149° C. (300° F.), and typically from about 121° C. (250° F.) to about 143° C. (290° F.), with a representative value being 130° C. (266° F.). Diesel fuel boiling-range hydrocarbons and jet fuel boiling-range hydrocarbons may have an initial boiling point temperature in the range from about 120° C. (248° F.) to about 160° C. (320° F.)), with a representative value being 149° C. (300° F.). The distillation end point temperature of diesel fuel boiling-range hydrocarbons is generally in the range from about 300° C. (572° F.) to about 400° C. (752° F.)), with a representative value being 370° C. (698° F.). These initial and end point temperatures, which are also characteristic of hydrocarbons in respective naphtha, gasoline, diesel fuel, and jet fuel fractions obtained from crude oil fractionation, may be measured according to ASTM D86, with the end point being the 95% recovery value.

"Higher hydrocarbons," relative to methane, include hydrocarbons having two or more carbon atoms, such ethane, propane, butane, etc. "$C_4^+$ hydrocarbons," as understood in the art, refer to hydrocarbons having four or more carbon atoms, which are readily condensable. Of the $C_4^+$ hydrocarbons, $C_4$-$C_{10}$ hydrocarbons are of particular interest for their use in transportation fuels, e.g., as a source of gasoline boiling-range hydrocarbons, diesel fuel boiling-range hydrocarbons, and jet fuel boiling-range hydrocarbons as described above. Of the $C_4^+$ hydrocarbons, $C_6$-$C_{10}$ hydrocarbons are of particular interest for their use as chemical products, such as aromatic hydrocarbon products including benzene, toluene, xylenes, and alkylbenzenes. Desired fractions, from which the higher hydrocarbons (or from which larger fractions, such as $C_6$-$C_{10}$ hydrocarbons) may be separated therefore include a purified benzene fraction, a purified toluene fraction, a purified xylene fraction (which may be further separated and/or isomerized to obtain a desired xylene isomer, e.g., para-xylene), and a purified alkylbenzene fraction.

As used herein, the term "substantially all" means "at least 95%," and the term "substantially complete" means "at least 95% complete." The term "predominantly" means "at least 50%."

Representative processes comprise feeding at least a portion of the methane-containing feedstock to a hydrogenation/oligomerization reactor to suppress a methane re-formation reaction and thereby increase a selectivity to, and/or yield of, $C_4^+$ hydrocarbons (i.e., the $C_4^+$ hydrocarbon-containing fraction of the higher hydrocarbons, which may be all or substantially all of the higher hydrocarbons), in an oligomerization effluent of the hydrogenation/oligomerization reactor, which is obtained from oligomerization of $CS_2$. The selectivity increase with respect to this reactor may, for example, be measured relative to a comparable base-case in which all of the methane-containing feedstock is fed to a sulfur oxidation reactor, upstream of the hydrogenation reactor. The selectivity to the $C_4^+$ hydrocarbons, with respect to the hydrogenation/oligomerization reactor, refers to the weight percentage of the carbon in $CS_2$, fed to this reactor, which becomes converted to $C_4^+$ hydrocarbons in the effluent of this reactor. In representative embodiments, the selectivity to $C_4^+$ hydrocarbons in the hydrogenation/oligomerization reactor may be increased, relative to the base case, by at least 2% (e.g., from 2% to 35%), by at least 5% (e.g., from 5% to 30%), or by at least 8% (e.g., from 8% to 25%). As the conversion of $CS_2$ in the hydrogenation/oligomerization reactor is, in preferred embodiments, substantially complete, substantially all of the same increases in the yield (the product of conversion and selectivity) of $C_4^+$ hydrocarbons in the hydrogenation/oligomerization reactor, relative to the base case, may be realized. These increases in selectivity and yield are namely the differences (rather than percentages of increases) between selectivities and yields obtained for processes as described herein, and those obtained for the comparable base-cases.

Particular processes may further comprise recycling a recycle gas stream comprising both $CH_4$ and $H_2S$ to a sulfur oxidation reactor positioned upstream of the hydrogenation/oligomerization reactor. The recycle gas stream may comprise at least a portion, and preferably substantially all, of an $H_2S/CH_4$ stream that is separated from a vapor product of the oligomerization effluent of the hydrogenation/oligomerization reactor. The processes may otherwise, but preferably in addition, comprise recycling, to the hydrogenation/oligomerization reactor, at least a portion of a hydrogen product stream that is separated from the vapor product of the oligomerization effluent.

Further embodiments of the invention relate to a process for converting a methane-containing feedstock to higher hydrocarbons (e.g., $C_4^+$ hydrocarbons), in which the process comprises continuously recycling $H_2S$ in an $H_2S$ recycle loop. This $H_2S$ recycle loop may be defined by (i) a recycle gas stream, comprising both $CH_4$ and $H_2S$, to a sulfur oxidation reactor, (ii) a sulfur oxidation effluent to a hydrogenation/oligomerization reactor, (iii) a hydrogenation/oligomerization effluent to a separation stage for condensing at least a portion of the higher hydrocarbons (e.g., as a liquid hydrocarbon product), and (iv) an $H_2S/CH_4$ stream that is separated, in the separation stage, from a vapor product of the effluent of the hydrogenation reactor. The recycle gas stream comprises at least a portion of the $H_2S/CH_4$ stream, thereby completing the loop. Advantageously, as described above, the continuous recycle of $H_2S$ in the $H_2S$ recycle loop maintains this valuable sulfur-containing compound, which serves as a carrier of the sulfur for sulfur oxidation (i.e., soft oxidation) of methane. Sulfur losses, as well as the requirements for handling $H_2S$ (which is both corrosive and toxic), are thereby minimized. According to representative embodiments, for example, sulfur is added to the process (e.g., added to the $H_2S$ recycle loop at any of the streams (i), (ii), (iii), and/or (iv) defining this loop, as described above) at a makeup rate of less than 2000 grams (e.g., from 2 grams to less than 2000 grams) S per million grams of the $C_4^+$ hydrocarbons produced. In preferred embodiments, the makeup rate is less than 1000 grams (e.g., from 2 grams to less than 1000 grams), less than 500 grams (e.g., from 2 grams to less than 500 grams), or even less than 100 grams (e.g., from 2 grams to less than 100 grams) S per million grams of the $C_4^+$ hydrocarbons produced. This makeup rate, in terms of grams of elemental sulfur (S) added per million parts of the $C_4^+$ hydrocarbons produced, may also be equivalently expressed in terms of "parts by weight S per million parts by weight of the $C_4^+$ hydrocarbons."

According to any of the processes described herein, a sufficient methane partial pressure in the hydrogenation/oligomerization reactor, or in the second stage generally, may be maintained such that the undesirable re-formation of methane is suppressed, thereby increasing selectivity to $C_4^+$ hydrocarbons in this reactor or stage. Such methane partial pressure may be maintained, for example, by introducing at least a portion, and preferably substantially all, of the methane-containing feedstock to the second stage of the process, or more particularly, to an inlet to the hydrogenation/oligomerization reactor. At least a portion (e.g., at least 50%), or substantially all, of the methane-containing feedstock may otherwise, or in addition, be introduced to the sulfur oxidation effluent, or namely a point of mixing with the sulfur oxidation effluent. A representative methane partial pressure in the second stage, or more particularly in the hydrogenation/oligomerization reactor, sufficient to obtain the $C_4^+$ hydrocarbon selectivity and yield improvements described herein, is at least 10 kilopascals (10 kPa), for example from 10 kPa to 4.5 MPa or from 250 kPa to 4.5 MPa. This methane partial pressure may be at least 20 kPa (e.g., from 20 kPa to 3.5 MPa or from 500 kPa to 3.5 MPa), or at least 35 kPa (e.g., from 35 kPa to 3 MPa or from 1 MPa to 3 MPa).

According to any of the processes described herein, for example as a result of maintaining sufficient methane partial pressure in the hydrogenation/oligomerization reactor, or in the second stage generally, the selectivity to $C_4^+$ hydrocarbons may be at least 35%, for example from 35% to 95%. This selectivity may be at least 45% (e.g., from 45% to 70%), or at least 50% (e.g., from 50% to 65%). The same percentages, and ranges of percentages, apply to the yields of $C_4^+$ hydrocarbons in the hydrogenation/oligomerization reactor, or in the second stage generally, in view of the conversion of $CS_2$ in this reactor or stage being complete, or substantially complete.

First Reaction Stage

In representative embodiments, a first reaction stage is used to perform sulfur oxidation, such that this stage may alternatively be referred to as a sulfur oxidation stage. This stage may comprise one or more sulfur oxidation reactors, in which $CH_4$ in the methane-containing feedstock is reacted with $H_2S$ to form $CS_2$ according to the reaction:

$$2H_2S + CH_4 \rightarrow CS_2 + 4H_2 \qquad (1).$$

In a preferred embodiment, the first reaction stage comprises a single sulfur oxidation reactor. The $CH_4$ may be fed to the sulfur oxidation stage in a recycle gas comprising recycle $CH_4$ and recycle $H_2S$. Amounts of $H_2S$ needed to sustain the process, for example to provide a makeup rate of sulfur to compensate for steady-state losses of the sulfur-containing compound as described above, may be introduced to this recycle gas in the form of $H_2S$ that is generated from an $H_2S$-precursor, such as an organic sulfide (e.g., dimethyl disulfide, DMDS) or even $CS_2$, which decomposes at elevated temperatures and in a hydrogen atmosphere, to form the reactant $H_2S$. For example, DMDS decomposes to form $H_2S$ and $CH_4$ in the recycle gas, according to the reaction:

$$CH_3S_2CH_3 + 3H_2 \rightarrow 2\ CH_4 + 2\ H_2S \qquad (2).$$

An $H_2S$-precursor may also be used to provide an initial $H_2S$ charge rate that is significantly higher, relative to the makeup rate at steady state. The initial charge rate can establish a concentration of $H_2S$ in the recycle gas, during a startup period that precedes the introduction (feeding) of the methane-containing feedstock to the process. According to alternative embodiments, the $H_2S$ or an $H_2S$-precursor may be introduced at various introduction locations described herein, such as the possible feedstock introduction locations, described below. Suitable $H_2S$ precursors are preferably organic sulfur-containing liquids, such as DMDS, that facilitate handling of the process sulfur requirements.

Suitable conditions in the first stage, e.g., sulfur oxidation reactor conditions, may include a temperature from 1000° C. to 1200° C., and typically from 1050° C. to 1150° C., and a total absolute pressure from 350 kPa to 6 MPa, and typically from 350 kPa to 4 MPa. These conditions may also include sufficient hydrogen partial pressure to maintain catalyst activity, by preventing side reactions that lead to coke formation. Representative hydrogen partial pressures in the first stage are from 100 kPa to 3.5 Mpa, and typically from 100 kPa to 2.5 MPa.

By having a substantial molar excess of $H_2S$ in the first stage, conversion of $CH_4$ to $CS_2$ may be at least 90% in this stage, for example the conversion is typically at least 95% and often at least 98%. Conditions in the first stage may therefore include a molar ratio of $H_2S$ to $CH_4$ in the recycle gas, or otherwise in the combination of the recycle gas and any other gas stream (e.g., a portion of the methane-containing feedstock) that is fed to the first stage, from 1:1 to 4:1, and typically from 2.5:1 to 4:1 (i.e., in excess of the stoichiometric ratio according to reaction (1) above). Stated otherwise, the conditions may include a first stage inlet $H_2S/CH_4$ molar ratio or sulfur oxidation reactor inlet $H_2S/CH_4$ molar ratio in these ranges. As a result of high conversion in the first stage, the methane partial pressure in the sulfur oxidation effluent (i.e., the effluent of the first stage prior to being mixed with any portion of the methane-containing feedstock that would increase the methane partial pressure in the resulting, combined stream) may be low, for example from 0 kPa to less than 10 kPa.

A sulfur oxidation reactor in the first stage may contain a sulfur oxidation catalyst comprising a sulfur oxidation active metal, or a compound of a sulfur oxidation active metal, wherein the sulfur oxidation active metal is selected from the group consisting of Pd, Mo, Cr, Ce, Pt, Ni, Rh, W, and Li. Combinations of these metals and/or metal compounds may also be used. Normally, in view of the significant concentration of $H_2S$ to which the sulfur oxidation catalyst is exposed, the sulfur oxidation active metal may be in its sulfided form, i.e., the sulfur oxidation catalyst may contain a metal sulfide compound of any one or more of these sulfur oxidation active metals. The sulfur oxidation active metal(s) may be supported on a suitable support material that is refractory to the conditions in the sulfur oxidation reactor. Representative support materials include alumina, silica, titania, and zirconia. Specific examples of sulfur oxidation catalysts include Pd or PdS that is supported on zirconia ($Pd/ZrO_2$ or $PdS/ZrO_2$); Pt, Ni, or Rh that is supported on alumina ($Pt/Al_2O_3$, $Ni/Al_2O_3$, or $Rh/Al_2O_3$); $MoS_2$; PdS; $Cr_2S_3$; CeS; $WS_2$; and $LiS_2$. Preferred catalysts for use in the sulfur oxidation reactor include $Pd/ZrO_2$ and $MoS_2$.

The conversion of methane by soft oxidation to $CS_2$, occurring in the first-stage, is endothermic. Process heat, which is supplied at the very high temperatures described above for the first stage, may be obtained from the combustion of at least a portion of a hydrogen product of the process, and, according to more particular embodiments, at least a portion (e.g., all or substantially all), of a net hydrogen production stream, as described herein. The combustion of this readily available product is useful in locations lacking an accessible utility for transporting the net hydrogen produced for a more valuable end use (e.g., to a refinery). In a representative embodiment, at least 80% of the heat required in the first stage is provided from hydrogen combustion. Alternatively, if all of the heat required in the first stage is provided in this manner, according to preferred embodiments, then advantageously no additional heat is required, i.e., the process may be operated with no external source of heat, such as external fuel, and with no emission of $CO_2$.

A sulfur oxidation reactor in the first stage is normally subjected to severe operating conditions, including the temperatures and pressures as described above, in addition to a high partial pressure of hydrogen sulfide, for example generally greater than 350 kPa. Representative construction materials for the sulfur oxidation reactor will therefore require resistance to corrosion under these first stage operating conditions. A vessel of the first stage reactor may comprise, for example, an alloy of iron, chromium, and aluminum, in which chromium and aluminum are present in amounts by weight of the alloy of 20%-30% and 4-7.5%, respectively. A vessel of the first stage reactor may alternatively comprise an alloy of nickel, cobalt, and chromium, and optionally other alloyed elements. For example, according to one such alloy, cobalt, chromium, silicon, manganese, titanium, and carbon are present in amounts of at least 29%, at least 28%, at least 2.75%, at least 0.5%, and least 0.5% and at least 0.05%, respectively, be weight of the alloy, together with nickel. According to another embodiment, a vessel of the first stage reactor may comprise an alloy having a large proportion (e.g., greater than 50% by weight of the alloy) of niobium or of molybdenum. Pure niobium or molybdenum may also be used. According to yet another embodiment, a vessel of the first stage reactor may comprise a highly temperature-resistant alloy, in order to provide sufficient mechanical strength, and this alloy may optionally be plated, on a surface facing the interior of the vessel, with a noble metal such as platinum or palladium for corrosion resistance. According to still another embodiment, a vessel of the first stage reactor may comprise a corrosion-resistant inner shell, facing the interior of the vessel, that is capable of resisting the corrosive atmosphere and high temperature of the first stage, and an outer shell, toward or facing the exterior of the vessel, of sufficient mechanical strength to contain the pressure in the first stage.

Second Reaction Stage

In representative embodiments, a second reaction stage is used to perform oligomerization of the $CS_2$ that is produced in the first stage, according to reaction (1) above. Because oligomerization occurs in conjunction with hydrogen consumption, the second stage may alternatively be referred to as a "hydrogenation/oligomerization" stage. This stage may comprise one or more hydrogenation/oligomerization reactors, in which $CS_2$ in the effluent from the first stage (e.g., a sulfur oxidation effluent) is reacted with $H_2$ to form higher hydrocarbons ($-[CH_2]-$) according to the reaction:

$$CS_2 + 3H_2 \rightarrow [-CH_2-] + 2H_2S \quad (3).$$

In a preferred embodiment, the second reaction stage comprises a single hydrogenation/oligomerization reactor. Also, according to other preferred embodiments as described above, the methane partial pressure in the second stage (e.g., at an inlet to a hydrogenation/oligomerization reactor) may be increased by feeding at least a portion, and preferably substantially all, of the methane-containing feedstock to an inlet of the second stage or to a point of mixing with the sulfur oxidation effluent. Therefore, the combined second stage feed, including the sulfur oxidation effluent being fed to the second stage, together with any portion of the methane-containing feedstock that is co-fed to the second stage or upstream of the second stage, may include methane at a concentration of at least 5 vol-%, such as from 5 vol-% to 50 vol-%. Typically, this concentration is at least 7 vol-% (e.g., from 7 vol-% to 35 vol-%), and often at least 10 vol-% (e.g., from 10 vol-% to 25 vol-%). Conditions in the second stage may therefore include these volume percentages of methane at the inlet to a hydrogenation/oligomerization reactor. Representative volume percentages of $H_2$, $H_2S$, and $CS_2$ at the inlet to this reactor are, respectively, 45 to 70 vol-%, 8 to 25 vol-%, and 10 to 25 vol-%. Representative methane partial pressures in the second stage, and accompanying increases in selectivity to $-[CH_2]-$, are described above. These advantages may be associated with suppression of undesired re-formation of methane, according to the reverse of reaction (1) above, occurring in the second stage.

Alternatively or in conjunction with reaction (3) above, the formation of higher hydrocarbons may occur through formation of intermediate methanethiol ($CH_3SH$), according to the reactions:

$$CH_4 + CS_2 + H_2 \rightarrow 2CH_3SH + H_2S \quad (4) \text{ and}$$

$$2CH_3SH \rightarrow -[CH_2]- + 2H_2S \quad (5).$$

Suitable conditions in the second stage, e.g., hydrogenation/oligomerization reactor conditions, may include a temperature from 250° C. to 500° C., and typically from 350° C. to 400° C. The total absolute pressure and hydrogen partial pressure in the second stage may be within the same ranges as described above with respect to the first stage (e.g., a total absolute pressure from 350 kPa to 6 MPa, and typically from 350 kPa to 4 MPa, and a hydrogen partial pressure from 100 kPa to 3.5 Mpa, and typically from 100 kPa to 2.5 MPa). Preferably, the total absolute pressure in the second stage is lower than that of the first stage, such that process flow from the first to the second stage can be maintained without intermediate compression. The pressure drop from the first stage to the second stage is typically a nominal value (e.g., from 35 to 350 kPa), associated with head losses through process equipment. As in the first stage, elevated hydrogen partial pressure is preferred in the second stage (e.g., in the hydrogenation/oligomerization reactor) to minimize catalyst coking and thereby maintain catalyst activity. Other conditions in the second stage may include a molar ratio of $H_2$ to $CS_2$ in the combined second stage feed, including the sulfur oxidation effluent being fed to the second stage, together with any portion of the methane-containing feedstock that is co-fed to the second stage or upstream of the second stage (e.g., any portion fed to an inlet of the second stage or to a point of mixing with the sulfur oxidation effluent) from 1:1 to 10:1, and typically from 3:1 to 5:1. Accordingly, conditions in the second stage may include a second stage inlet $H_2/CS_2$ molar ratio or hydrogenation/oligomerization reactor inlet $H_2/CS_2$ molar ratio, within these ranges. In this regard, it can be appreciated that any co-fed, methane-containing feedstock normally will not appreciably impact this $H_2/CS_2$ molar ratio.

A hydrogenation/oligomerization reactor in the second stage may contain a hydrogenation/oligomerization catalyst comprising a hydrogenation/oligomerization active metal, or a compound of a hydrogenation/oligomerization active metal, wherein the hydrogenation/oligomerization active metal is selected from the group consisting of Co, Ga, Ni, and Mo. Combinations of these metals and/or metal compounds may also be used. Normally, in view of the significant concentration of $H_2S$ to which the hydrogenation/oligomerization is exposed, the hydrogenation/oligomerization active metal may be in its sulfided form, i.e., the hydrogenation/oligomerization catalyst may contain a metal sulfide compound of any one or more of these hydrogenation/oligomerization active metals. The hydrogenation/oligomerization active metal(s) may be supported on a suitable support material that is refractory to the conditions in the hydrogenation/oligomerization reactor and/or otherwise lends desired catalytic activity (e.g., acidity). Representative support materials include zeolitic and non-zeolitic molecular sieves, examples of which are, respectively, ZSM-5 and AMS-1B borosilicate. These materials are described, respectively, in U.S. Pat. No. 3,702,886 and U.S. Pat. No. 4,514,516. Specific examples of hydrogenation/oligomerization catalysts include Co that is supported on ZSM-5, in combination with $MoS_2$ (i.e., Co/ZSM-5+$MoS_2$); Ga that is supported on ZSM-5 (Ga/ZSM-5); and Co that is supported on AMS-1B borosilicate, in combination with $MoS_2$ (i.e., Co-AMS-1B/borosilicate+$MoS_2$).

Separation Stage

Higher hydrocarbons (e.g., $C_4^+$ hydrocarbons) may be recovered from the second stage effluent (e.g., the hydrogenation/oligomerization reactor effluent) by condensing all, or substantially all, of these hydrocarbons into a liquid product and separating, from this liquid product, a vapor product comprising $H_2$ and $H_2S$ present in the second stage effluent (i.e., comprising second stage $H_2$ and second stage $H_2S$). The condensing may be performed by simply cooling the second stage effluent, for example to a temperature of 30° C. or less, and more typically 25° C. or less, for example to a temperature between 10° C. and 25° C., characteristic of process cooling water. Alternatively, a chiller or chilled adsorber may be used to achieve lower temperatures, for example between −5° C. and 10° C. The condensing may involve a single vapor-liquid equilibrium stage of separation, for example by being performed in a flash drum, or otherwise multiple vapor-liquid equilibrium stages of separation in a single vessel (e.g., in the case of a stripper) or multiple vessels, such as in the case of a secondary knockout drum for removing higher hydrocarbons that may be carried (e.g., by entrainment) into a vapor phase of a primary flash drum. Alternative to, or in combination with, the use of a secondary knockout drum, such entrainment may be reduced using a suitable coalescer in an upper section of the primary flash drum.

The separated vapor product, following condensation of higher hydrocarbons, may then be further separated to provide a hydrogen product stream that is enriched in $H_2$ concentration, relative to the vapor product, and an $H_2S/CH_4$ stream that is depleted in $H_2$ concentration, relative to the vapor product. This $H_2/H_2S$ separation may be performed using a sour gas pressure swing adsorber (PSA) that may also preferentially separate not only methane, but other non-condensable gases (e.g., ethane) into the $H_2S/CH_4$ stream. According to a representative separation by PSA, the concentration of $H_2S$ in the hydrogen product stream is less than 10 ppm (e.g., from 0.1 ppm to less than 10 ppm) and recovery of $H_2S$ in the $H_2S/CH_4$ stream is greater than 99% (e.g., from 99% to 99.999%). For a given adsorbent, the degree of $H_2S$ removal from the hydrogen product and degree of recovery of $H_2S$ in the $H_2S/CH_4$ stream can be varied by manipulating operating parameters, such as the number of separation stages.

The liquid product, into which the higher hydrocarbons (e.g., $C_4^+$ hydrocarbons) are condensed, may be further separated to remove impurities such as dissolved $H_2S$ and/or to resolve any of the various fractions described above, including gasoline boiling-range hydrocarbons, diesel fuel boiling-range hydrocarbons, and jet fuel boiling-range hydrocarbons, which may be used as end products or otherwise as blending components. For example, such gasoline, diesel fuel, and/or jet fuel fractions may be blended with a viscous hydrocarbon-containing liquid, comprising relatively higher molecular weight hydrocarbons and/or having a relatively higher viscosity and boiling point range, to obtain a blended liquid stream having a viscosity lower than that of the viscous hydrocarbon-containing liquid. Further separation of the higher hydrocarbons may be performed using a single vapor-liquid equilibrium stage of separation, but such separation is more preferably performed using multiple vapor-liquid equilibrium stages of separation, for example in one or more stripper and/or distillation columns. In a particular embodiment, a portion of the methane-containing feedstock is added to a stripper column to remove residual $H_2S$ that is dissolved in the liquid product, prior to fractionation of the liquid product in a distillation column to obtain desired fractions, including those described herein.

Representative Embodiment

The flowscheme of FIG. 1 illustrates a representative two-stage process, for the conversion of methane in a methane-containing feedstock to higher hydrocarbons. The illustrated process comprises feeding a recycle gas stream 27, comprising recycle $CH_4$ and recycle $H_2S$, to a sulfur oxidation stage or reactor 100. First stage heater 15 is used to obtain the high temperatures, described above, as needed to perform sulfur oxidation in this stage or reactor. A least a portion, and preferably substantially all, of the recycle $CH_4$ is converted by reaction with the recycle $H_2S$, to provide a sulfur oxidation effluent 11 comprising $CS_2$. As described above, the $H_2S$ is normally provided to sulfur oxidation stage or reactor 100 with recycle gas stream 27, at a molar excess of $CH_4$, and preferably even in an excess of the stoichiometric (2:1 $H_2S:CH_4$) molar ratio according to reaction (1) above, in order to ensure that $CH_4$ is the limiting reagent and thereby promote its conversion to $CS_2$. The illustrated process further comprises feeding at least a portion of, and preferably substantially all, of sulfur oxidation effluent 11 to a second stage or reactor 200 (e.g., a hydrogenation/oligomerization stage or reactor), preferably following cooling in sulfur oxidation effluent cooler 45 to obtain the temperatures described above, as needed to perform hydrogenation/oligomerization in this stage or reactor. Following conversion of at least a portion of the $CS_2$ to $C_4^+$ hydrocarbons, a second stage effluent 13 (e.g., a hydrogenation/oligomerization effluent, for example an effluent of a hydrogenation/oligomerization reactor) is provided. Second stage effluent 13 comprises the $C_4^+$ hydrocarbons, together with second stage $H_2$ and second stage $H_2S$, which are also contained in second stage effluent 13. The illustrated process further comprises introducing second stage effluent 13 to separation stage 300, following cooling in second stage effluent cooler 25, to perform various separations as described above. These may include condensing, from second stage effluent 13, at least a portion, and preferably substantially all, of the $C_4^+$ hydrocarbons in this stream into a liquid product 19 that is separated from vapor product 17, comprising at least a portion, and preferably substantially all, of the second stage $H_2$ and the second stage $H_2S$ contained in second stage effluent 13.

The illustrated process further comprises separating at least a portion, and preferably substantially all, of vapor product 17 to provide a hydrogen product stream 33. This separation is performed in vapor product separation stage 400, which may include, for example, one or more vessels housing an adsorbent (e.g., in the case of separation by pressure swing adsorption (PSA)) or one or more vessels housing a membrane or multiple membranes. A first portion of hydrogen product stream 33 may be removed from the process as a net hydrogen production stream 47, and a second portion (i.e., a recycle portion) of hydrogen product stream 33, may be recycled to the process, using hydrogen recycle compressor 35, as a hydrogen recycle stream 49. Hydrogen product stream 33 is enriched in $H_2$ (i.e., has a higher $H_2$ concentration) relative to vapor product 17. Separating vapor product 17, in vapor product separation stage 400, also provides an $H_2S/CH_4$ stream 27' that is depleted in $H_2$ (i.e., has a lower $H_2$ concentration) relative to vapor product 17. At least a portion, and preferably substantially all, of $H_2S/CH_4$ stream 27' forms all or part of recycle stream 27. Stated otherwise, recycle gas stream 27 comprises at least a portion, and preferably substantially all, of $H_2S/CH_4$ stream 27'. For example, according to the illustrated process, the portion 27" of $H_2S/CH_4$ stream 27' that is not removed in bleed stream 51, is fed to $H_2S/CH_4$ recycle compressor 55 and forms recycle gas stream 27. According to some embodiments, bleed stream 51 may optionally be used, intermittently or continuously, to limit the accumulation of non-condensable gases in recycle gas stream 27, such as hydrocarbons (e.g., ethane) produced in the process and/or impurities (e.g., CO, $CO_2$) entering the process in the methane-containing feedstock.

All, substantially all, or a portion, of hydrogen recycle stream 49 may be introduced as a second stage hydrogen-containing reactant stream 21 to second stage or reactor 200 for sustaining the hydrogen/oligomerization occurring in this stage, as described above. Also, an $H_2S$-precursor decomposition stream 23 may optionally be fed, as a portion of hydrogen recycle stream 49, to $H_2S$-precursor decomposition stage 500. At this stage, an $H_2S$-precursor stream 29 (e.g., comprising DMDS or other $H_2S$-precursor as described above) is contacted with hydrogen that is contained in $H_2S$-precursor decomposition stream 23, to a provide makeup $H_2S$ stream 31, which is fed to the process at a makeup rate to compensate for minor losses of $H_2S$ (e.g., contained in bleed stream 51 and in net hydrogen production stream 47, and/or dissolved in liquid product 19), as described above.

Certain advantages are gained, as described above and according to particular embodiments of the invention, by introducing the methane-containing feedstock at one or more feedstock introduction locations in the process, other than entirely to the sulfur oxidation stage and/or a point upstream of the sulfur oxidation stage. According to the illustrated process, possible feedstock introduction locations for methane-containing feedstock 10 include, (i) an inlet 12 to the sulfur oxidation stage or reactor 100, (ii) an inlet 14 to the second stage or reactor 200, (iii) a point of mixing 16 with the sulfur oxidation effluent 11, (iv) a point of mixing 18 with the second stage effluent 13, (v) a point of mixing 20 with the vapor product 17, and/or (vi) a point of mixing 22 with the recycle gas stream 27, which may comprise substantially all of the $H_2S/CH_4$ stream 27' (or a non-bleed portion 27" thereof). Other feedstock introduction locations can include a point of mixing 24 with the second stage hydrogen-containing reactant stream 21 and/or even separation stage 300. For example, a methane-containing feedstock introduction location at separation stage 300 may be suitable for stripping $H_2S$ from condensed higher hydrocarbons, to provide liquid product 19 with reduced $H_2S$ content and a stripper off gas 41 that may be added to $H_2S/CH_4$ stream 27'. According to preferred embodiments, the one or more feedstock introduction locations includes inlet 14 to the second stage or reactor 200 and/or point of mixing 16 with the sulfur oxidation effluent 11.

The flowscheme of FIG. 2 illustrates a representative separation stage 300, for processing second stage effluent 13. According to this illustrated embodiment, second stage effluent 13 is fed to primary flash drum 310 to separate, in a vapor-liquid equilibrium separation stage, flash drum overhead vapors 53 from flash drum bottoms liquid 59. A flash drum overhead vapor compressor 65 may be used to re-compress flash drum overhead vapors 53, prior to introduction to secondary knockout vessel 330. The overhead fraction from secondary knockout vessel 330 may be removed from separation stage 300 as vapor product 17, and the bottoms fraction 57 from secondary knockout vessel 330 may be combined with flash drum bottoms liquid 59 and introduced as condensed higher hydrocarbons 61 to product stripper 320, used to separate gases, including dissolved $H_2S$, from condensed higher hydrocarbons 61 and provide both liquid product 19 and stripper off gas 41, described above, which may be removed from separation stage 300. Product stripper 320 may be used to perform multiple vapor-liquid equilibrium separation stages, and at least a portion of the methane-containing feedstock 10 may optionally be added to product stripper 320 to facilitate the desired separation of $H_2S$ into stripper off gas 41. Liquid product 19 may be fed to distillation column 355, used to perform multiple vapor-liquid equilibrium separation stages and thereby resolve desired product fractions as described above, for example gasoline fraction 37 and diesel fuel fraction 39.

Overall Process

As is apparent from the combination of first stage and second stage reactions (1) and (3) above, processes described herein may be used to perform an overall reaction, with continuous recycle of $H_2S$ in a recycle gas stream, of:

$$CH_4 \rightarrow -[CH_2]- + H_2 \qquad (6),$$

whereby the process converts substantially all of the carbon in methane to higher hydrocarbons and also converts substantially all of the hydrogen in methane to a net hydrogen production stream. Whereas the "per-pass" yield of higher hydrocarbons over a given stage (e.g., the second stage) may be limited by undesired reactions, such as the re-formation of methane as described above, the overall yield of the process may be at least 95% and may approach 100% if, in the recycle gas, $H_2S$ is continually recycled and $CH_4$ is recycled to extinction. As described above, process economics are significantly improved by increasing the per-pass selectivity to higher hydrocarbons (—[$CH_2$]—) in the second stage, leading to a reduced requirement for recycle gas circulation, which in turn beneficially reduces both capital (e.g., process equipment) and operating (e.g., utility) costs. Representative processes, in which methane is converted to higher hydrocarbons, advantageously transfer carbon and chemical energy in the methane-containing feedstock, of a relatively low bulk density, to a liquid product containing higher hydrocarbons, of a relatively high bulk density that can be more easily transported than the methane-containing feedstock. The first stage and second stage reactions (1) and (3) above may be performed in a single vessel (e.g., in separate zones within a vessel), although they are typically performed in separate vessels, or reactors, that may reside in separate stages of the processes in which specific and different conditions are maintained to promote the desired sulfur oxidation and hydrogenation/oligomerization.

Processes as described herein may provide a number of products, such as a purified $CS_2$-containing product stream, recovered as a portion of the sulfur oxidation effluent, or a bleed stream, as described above, comprising light (non-condensable) hydrocarbons, such as ethylene and propylene, which are valuable, although not condensed into the liquid product and not useful as liquid hydrocarbon fuel.

Methane conversion to liquid fuels, as described herein, confers a very significant logistical benefit, since liquid fuels, because of their relatively greater bulk density, are far easier to transport over long distances than gaseous fuels. As a result, processes described herein allow for the economical use of supplies of "stranded" gas, such as remote natural gas wells or streams of renewable methane-containing gas from biomass digesters. According to particular embodiments, light hydrocarbon liquids obtained from processes described herein (e.g., gasoline, jet fuel, and/or diesel fuel fractions) may be blended with higher molecular weight hydrocarbons, such as those contained in crude oil. The resulting mixture may be less viscous than the higher molecular weight hydrocarbons would be in the absence of blending, thereby facilitating transport of the blend, particularly in the context of pipeline operations.

If all, or substantially all, of the carbon supplied to the process is transferred to the liquid product, and this carbon is of biological origin (with the possible exception of carbon in an $H_2S$-precursor such as DMDS that is needed to supply the process with sulfur), and the combustion of hydrogen is sufficient to meet the energy needs of the process, then the process provides a means whereby methane from renewable sources can be converted to a liquid product, and particularly liquid product fractions as described herein, without emitting carbon dioxide. That is, representative fractions, such as a gasoline fraction, a diesel fuel fraction, and/or a jet fuel fraction, may be produced with no or with negligible carbon footprint, based on a lifecycle assessment of the greenhouse gas (GHG) emission value, according to U.S. government accounting practices. The lifecycle greenhouse gas emission value may be measured based on $CO_2$ equivalents (e.g., grams (g) of $CO_2$-equivalents/megajoule (MJ) of energy or pounds (lb) of $CO_2$ equivalents/million BTU (mmBTU of energy, wherein 1 g $CO_2$-eq./MJ is about 2.33 lb $CO_2$-eq./mmBTU), as measured according to guidelines set forth by the Intergovernmental Panel on Climate Change (IPCC) and the U.S. federal government. Lifecycle assessment (LCA) values of emissions in terms of $CO_2$ equivalents, from raw material cultivation (in the case of plant materials) or raw material extraction (in the case of fossil fuels) through fuel combustion, can be calculated using SimaPro 7.1 software and IPCC GWP 100a methodologies.

Processes as described herein may also be used to obtain other valuable product streams, for example from the vapor product recovered downstream of the second stage. Otherwise, ethylene and other olefins may be separated and recovered from the liquid product and/or from the $H_2$, $H_2S$, $CH_4$, and other non-condensable gases recycled in the recycle gas to the first stage. Ethylene and other olefins may therefore be enriched in a separate product stream. Another desired product stream may comprise $CS_2$, for example a portion of this intermediate that is produced in the first stage and diverted to prevent its entry to the second stage. Once separated from the other process vapors, a product stream comprising $CS_2$ (e.g., enriched in $CS_2$ relative to the sulfur oxidation effluent) may comprise a separate product stream of the process.

Overall, aspects of the invention are directed to processes and systems for converting methane in a methane-containing feedstock to higher hydrocarbons, which may be of value as transportation fuels. Such processes and systems may advantageously exhibit improved process economics compared to known processes, by virtue of improving reaction selectivity to desired end products and/or recycling valuable materials, as described throughout the present disclosure. Those having skill in the art, with the knowledge gained from the present disclosure, will recognize that various changes can be made to these processes in attaining these and other advantages, without departing from the scope of the present disclosure. As such, it should be understood that the features of the disclosure are susceptible to modification, alteration, changes, or substitution without departing from the scope of this disclosure. The specific embodiments illustrated and described herein are for illustrative purposes only, and not limiting of the invention as set forth in the appended claims.

The invention claimed is:

1. A process for converting a methane-containing feedstock to $C_4^+$ hydrocarbons, the process comprising:
   (a) feeding a recycle gas stream comprising recycle $CH_4$ and recycle $H_2S$ to a sulfur oxidation stage to convert at least a portion of the recycle $CH_4$ and provide a sulfur oxidation effluent comprising $CS_2$;
   (b) feeding at least a portion of the sulfur oxidation effluent to a second stage to convert at least a portion of the $CS_2$ to the $C_4^+$ hydrocarbons and provide a second stage effluent comprising the $C_4^+$ hydrocarbons, second stage $H_2$ and second stage $H_2S$;
   (c) condensing, from the second stage effluent, at least a portion of the $C_4^+$ hydrocarbons into a liquid product that is separated from a vapor product comprising at least a portion of the second stage $H_2$ and the second stage $H_2S$;
   (d) separating at least a portion of the vapor product to provide a hydrogen product stream that is enriched in $H_2$ relative to the vapor product and an $H_2S/CH_4$ stream that is depleted in $H_2$ relative to the vapor product, wherein at least a portion of the $H_2S/CH_4$ stream forms all or part of the recycle gas stream.

2. The process of claim 1, wherein sulfur is added to the process at a makeup rate of less than 1000 parts by weight S per million parts by weight of the $C_4^+$ hydrocarbons.

3. The process of claim 1, wherein the second stage is operated with a selectivity to $C_4^+$ hydrocarbons of at least 40%.

4. The process of claim 1, further comprising introducing the methane-containing feedstock at one or more feedstock introduction locations selected from the group consisting of (i) an inlet to the sulfur oxidation stage, (ii) an inlet to the second stage, (iii) a point of mixing with the sulfur oxidation effluent, (iv) a point of mixing with the second stage effluent, (v) a point of mixing with the vapor product, (vi) a point of mixing with the $H_2S/CH_4$ stream, (vii) an inlet to a separation stage for condensing the liquid product in step (c), and (viii) combinations thereof.

5. The process of claim 4, wherein the one or more feedstock introduction locations include an inlet to the second stage or a point of mixing with the sulfur oxidation effluent.

6. The process of claim 4, wherein at least 50% of the methane-containing feedstock is fed to an inlet to the second stage or a point of mixing with the sulfur oxidation effluent.

7. The process of claim 1, wherein the second stage is operated under second stage conditions that include a methane partial pressure of at least 10 kPa.

8. The process of claim 1, wherein a combined second stage feed includes a concentration of methane of at least 5 vol-%.

9. The process of claim 1, wherein the sulfur oxidation stage includes a sulfur oxidation reactor containing a sulfur oxidation catalyst comprising a sulfur oxidation active metal, or a compound of a sulfur oxidation active metal, wherein the sulfur oxidation active metal is selected from the group consisting of Pd, Mo, Cr, Ce, Pt, Ni, Rh, W, and Li.

10. The process of claim 9, wherein the compound of the sulfur oxidation active metal is a sulfide of the sulfur oxidation active metal.

11. The process of claim 1, wherein the process further comprises introducing a second stage hydrogen-containing reactant stream to the second stage, wherein the second stage hydrogen-containing reactant stream comprises at least a recycle portion of the hydrogen product stream.

12. The process of claim 1, wherein the second stage includes a hydrogenation/oligomerization reactor containing a hydrogenation/oligomerization catalyst comprising a hydrogenation/oligomerization active metal, or a compound of a hydrogenation/oligomerization active metal, wherein the hydrogenation/oligomerization active metal is selected from the group consisting of Co, Ga, Ni, and Mo.

13. The process of claim 12, wherein the hydrogenation/oligomerization reactor is operated under hydrogenation/oligomerization reactor conditions that include a hydrogen partial pressure of at least 350 kPa.

14. The process of claim 1, wherein the methane-containing feedstock comprises methane that is derived from a renewable carbon source.

15. The process of claim 14, further comprising combusting at least a portion of the hydrogen product to provide heat that is transferred to (i) the recycle gas to the sulfur oxidation stage, (ii) the methane-containing feedstock being introduced at either the inlet to the sulfur oxidation stage or the point of mixing with the $H_2S/CH_4$ stream, or (iii) both (i) and (ii).

* * * * *